United States Patent [19]

Zenno et al.

[11] Patent Number: 5,288,623
[45] Date of Patent: Feb. 22, 1994

[54] PROCESS FOR SECRETORY PRODUCTION OF A CALCIUM-BINDING PROTEIN

[75] Inventors: Shuhei Zenno, Yokohama, Japan; Satoshi Inouye, San Diego, Calif.

[73] Assignee: Chisso Corporation, Osaka, Japan

[21] Appl. No.: 912,582

[22] Filed: Jul. 13, 1992

Related U.S. Application Data

[63] Continuation of Ser. No. 587,843, Sep. 25, 1990, abandoned.

[30] Foreign Application Priority Data

Oct. 26, 1989 [JP] Japan .................................. 1-279528

[51] Int. Cl.$^5$ ........................ C12N 15/62; C12N 15/70
[52] U.S. Cl. ................................ 435/69.7; 435/252.3; 435/320.1
[58] Field of Search .................. 435/69.7, 252.3, 320.1

[56] References Cited

U.S. PATENT DOCUMENTS 4,595,658  6/1986  Zinder et al. ........................ 435/68
4,839,293  6/1989  Cantor et al. ....................... 435/320

OTHER PUBLICATIONS

The EMBO J. vol. 6: 2835–2841, 1987, Mackman et al. Release of a chimeric protein into the medium from Escherichia coli using the –C-terminal secretion . . .
PNAS 87: 2047–2051, Mar. 1990, Casadei et al. Expression and secretion of aequorin as a chimeric antibody by means of a mammalian expression vector.
Anal. Biochem. 186: 14–18, Apr. 1990, Kobataké et al. Application of a fusion protein, Metapyrocatechase/-Protein A, to an Enzyme Immunoassay.
PNAS 82: 3154–3158, May 1985, Inouye et al. Cloning and sequence analysis of CDNA for the luminescent protein aequorin.
EMBO J, 4: 1075–1080, 1985, Nilsson et al. Immobilization and purification of enzymes with staphylococcal protein A gene fusion vectors.
EMBO J, 3: 2437–2442, Mar. 1984, Ghrayeb et al. Secretion cloning vectors in *Escherichia coli.*
J. Biochem. 105: 473–477, Mar. 1989, S. Inouye et al. Over expression and Purification of the Recombinant $Ca^{2+}$ Binding Protein, Apoaequorin.
Biochem. 26: 5239–5244, Aug. 1987, Moks et al. Expression of Human Insulin–like Growth Factor I in Bacteria: Use of Optimized Gene Fusion Vectors to Facilitate Protein Purification.

*Primary Examiner*—Robert J. Hill, Jr.
*Assistant Examiner*—John D. Ulm
*Attorney, Agent, or Firm*—Wenderoth, Lind & Ponack

[57] ABSTRACT

A process for secretory production of a calcium-binding protein very useful for producing heterogenic proteins in *Escherichia coli* according to gene recombinant technique is provided, which process comprises using *Escherichia coli* and using a secretory expression system with the promoter of lipoprotein and the gene of signal peptide of outer membrane protein A, according to recombinant DNA technique.

2 Claims, 17 Drawing Sheets

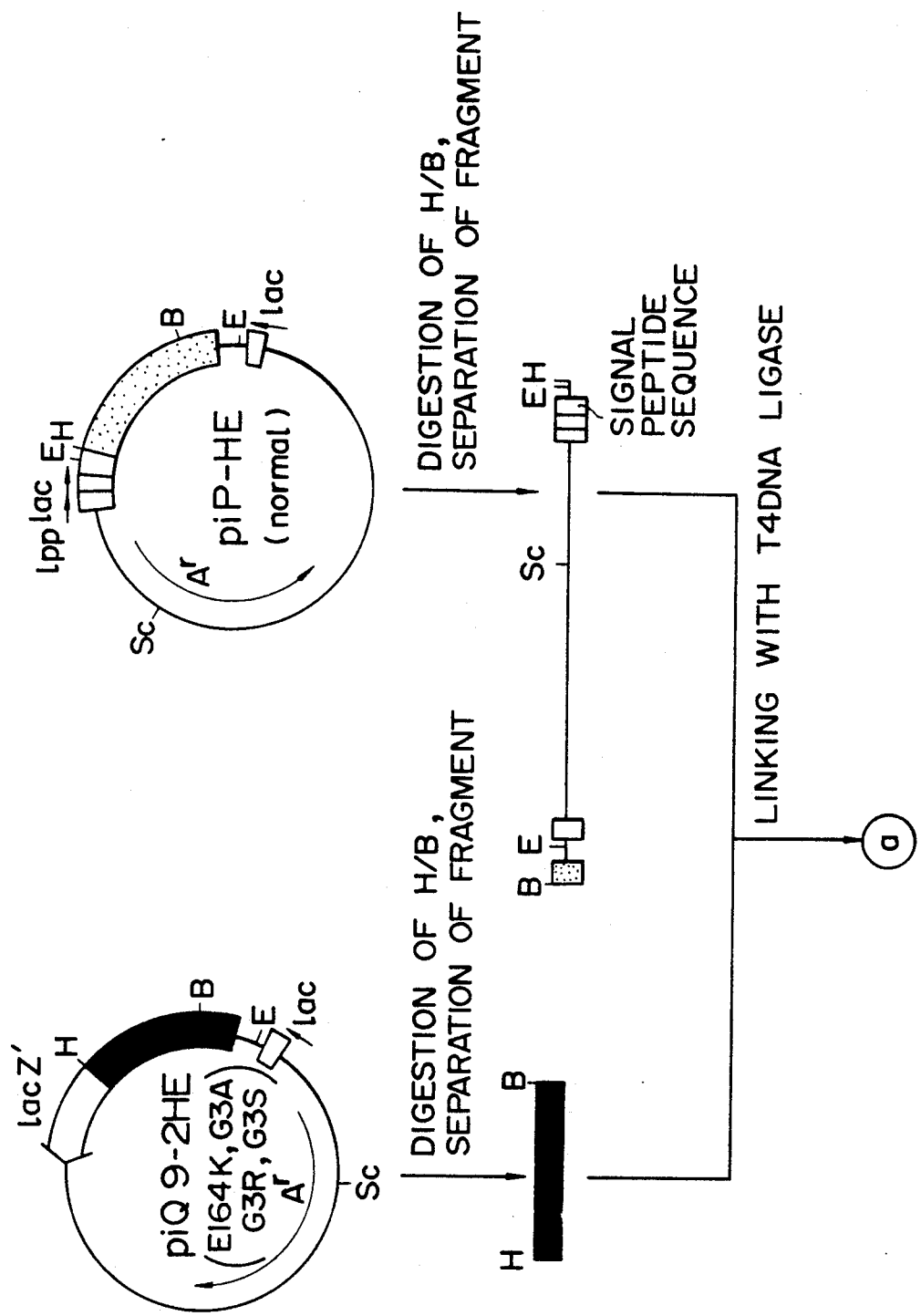

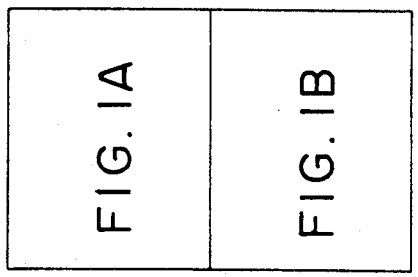
FIG. 1
| FIG. 1A |
| --- |
| FIG. 1B |
FIG. 1B
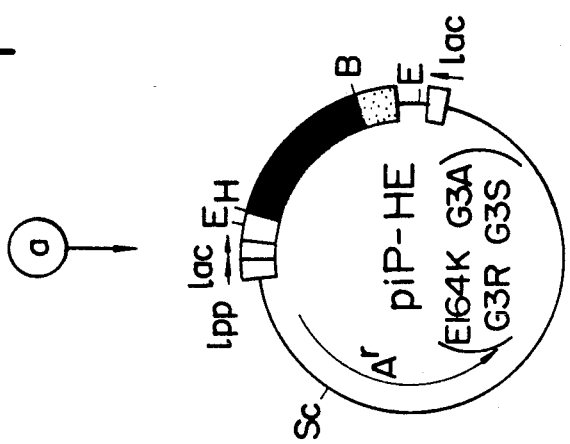
E : EcoR I
H : Hind III
B : BamH I
Sc : Sca I
lac : PROMOTER OF β-GALACTOSIDASE
lpp : PROMOTER OF LIPOPROTEIN
lacZ' : A PORTION OF β-GALACTOSIDASE GENE
▦ : NORMAL AEQUORIN GENE
■ : VARIANT AEQUORIN GENE

FIG. 2

EP HAND·DOMAIN 3

| AMINO ACID NO. | 153 | | | | 158 | | | | | | 164 |
|---|---|---|---|---|---|---|---|---|---|---|---|
| NORMAL | D | I | D | E | S | G | Q | L | D | V | D | E |
| E35K* | | | | | | | | | | | | K |
| G3A* | | | | | | A | | | | | | |
| G3R* | | | | | | R | | | | | | |
| G3S* | | | | | | S | | | | | | |

(NOTE) THE SYMBOL * INDICATES ONLY SUBSTUTED AMINO ACIDS AS COMPARED WITH NORMAL APOAEQUORIN.

(NOTE) THE SYMBOL "—" INDICATES APOAEQUORIN.

| FIG. 4A |
| FIG. 4B |
| FIG. 4C |

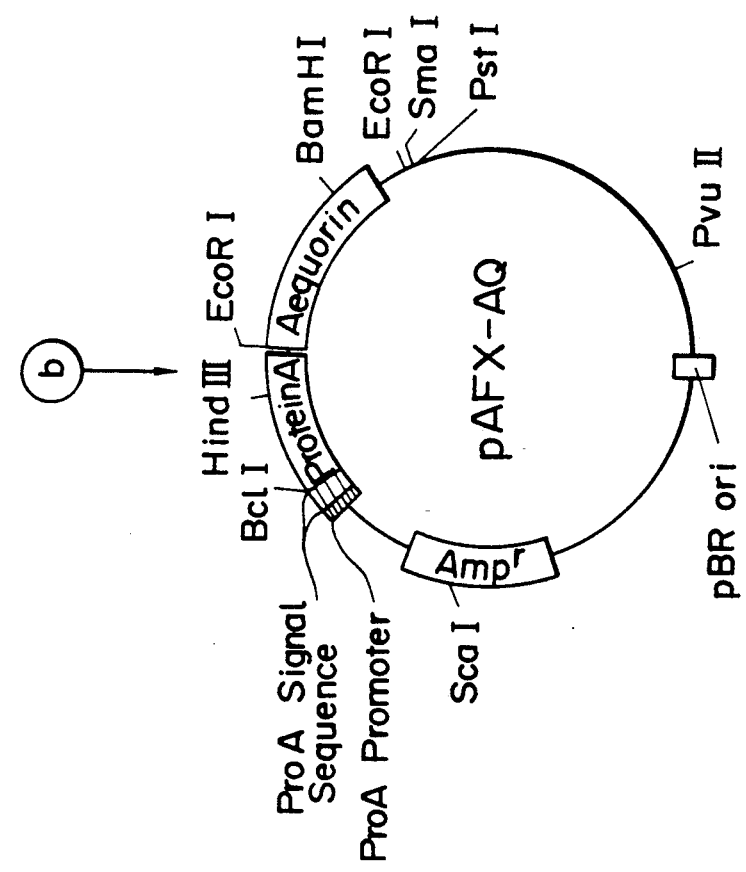

| FIG.5-2A |
| FIG.5-2B |
| FIG.5-2C |

PROCESS FOR SECRETORY PRODUCTION OF A CALCIUM-BINDING PROTEIN

This application is a continuation of now abandoned application Ser. No. 07/587,843 filed on Sep. 25, 1990, abandoned.

BACKGROUND OF THE INVENTION

1. Field of the Invention

This invention relates to a process for secretory production of a biogenic substance, which process is characterized by fusing useful proteins with a calcium-binding protein

2. Description of the Related Art

Photoprotein aequorin is a calcium-binding protein isolated from photogenic Aequorea living in the ocean near the suburbs of Friday Harbor Island, Washington State, U.S.A. As to the aequorin, apoaequorin as a protein portion and coelenterazine as a substrate portion form a complex in a medium containing molecular oxygen in nature, and the aequorin is characterized by causing luminescence by binding of calcium with the complex. By utilizing this luminescence, it is possible to measure calcium concentration.

The present inventors cloned cDNA of apoaequorin from photogenic Aequorea according to recombinant DNA technique and determined its primary structure (Japanese patent application laid-open No. Sho 61-135,586), and then using this cDNA and Escherichia coli as host, succeeded in intracellular and extracellular production of apoaequorin (Japanese patent application Nos. Sho 60-280,259 and Sho 61-249,098). Further, we prepared aequorin gene bound with the functional gene and succeeded in production of a fusion protein thereof (Japanese patent application No. Sho 62-196,031). Further, we developed a metal-detecting method by the use of luminescence of aequorin (Japanese patent application No. Sho 61-103,849). Further, we prepared aequorin gene bound with the gene of specifically bound protein and succeeded in production of fusion protein thereof (Japanese patent application No. Sho 63-308,424).

Further, in order to utilize the fusion protein for immunoassay of enzyme, we established a method for preparing a high purity specimen of the fusion protein (Japanese patent application No. Hei 1-69,862), and succeeded in practical application thereof to immunoassay (Japanese patent application No. Hei 1-74,742).

The present invention is based upon analysis of the mechanism of extracellular secretory production of apoaequorin in cells using Escherichia coli as host, and is directed to production of a useful biogenic substance utilizing the secretion production system.

Now, the usefulness of aequorin has been well known to persons skilled in the art, and by utilizing the luminescence of aequorin, it is possible to detect various substances. Namely, aequorin is applicable to all measurement systems such as immunoassay, DNA probe, biosensor, etc., and in view of the above-mentioned functions, aequorin can be expected to be useful as agents such as used in diagnostics.

In view of the above-mentioned technical situations, the present inventors have made extensive research, and as a result, have elucidated the mechanism of the secretory production of apoaequorin using Escherichia coli as host, and could have invented a process for secretory production of a useful biogenic substance.

SUMMARY OF THE INVENTION

As apparent from the foregoing, the object of the present invention is to provide a technique for secretory production of a useful biogenic substance using aequorin.

The present invention has the following constitutions (1) to (6):

(1) A process for secretory production of a calcium-binding protein, which process comprises using Escherichia coli as host and using a secretory expression system with the promoter of lipoprotein and the gene of signal peptide of outer membrane protein A, according to recombinant DNA technique.

(2) A process for secretory production of normal or variant apoaequorin, which comprises using a secretory expression system as set forth in item (1).

(3) A process for secretory production of a fusion protein of a calcium-binding protein with a biogenic substance, which process comprises using a secretory expression system as set forth in item (1).

(4) A process for secretory production of a fusion protein of apoaequorin with a biogenic substance, which process comprises using a secretory expression system as set forth in item (1).

(5) A process for secretory production of a calcium-binding protein and a biogenic substance, which process comprises using a secretory expression system as set forth in item (1) and inserting a sequence to be specifically cut by a chemical reagent or an enzyme into the fusion site of a fusion protein as set forth in item (3).

(6) A process for secretory production of apoaequorin and a biogenic substance, which process comprises using a secretory expression system as set forth in item (1) and inserting a sequence to be specifically cut by a chemical reagent or an enzyme into the fusion site of a fusion protein as set forth in item (4).

BRIEF DESCRIPTION OF THE DRAWINGS

FIGS. 1 to 7 each show an explanatory view of the present invention.

FIGS. 1A and B show the construction steps of secretory expression vector of variant aequorin.

FIG. 2 shows an amino acid sequence in the vicinity of amino acid-substituted site within a EF hand region of variant apoaequorin.

FIG. 3 shows analytical results of expression and secretion of apoaequorin according to SDS-PAGE.

FIGS. 4A to C, 5-1A to C and 5-2A to C each show the construction steps of the expression vector piP-AAQ2 or piP-AAQ4 of the fusion protein of protein A with apoaequorin.

FIG. 7 shows SDS-PAGE analysis of fusion protein.

DETAILED DESCRIPTION OF PREFERRED EMBODIMENTS

Figure 3:
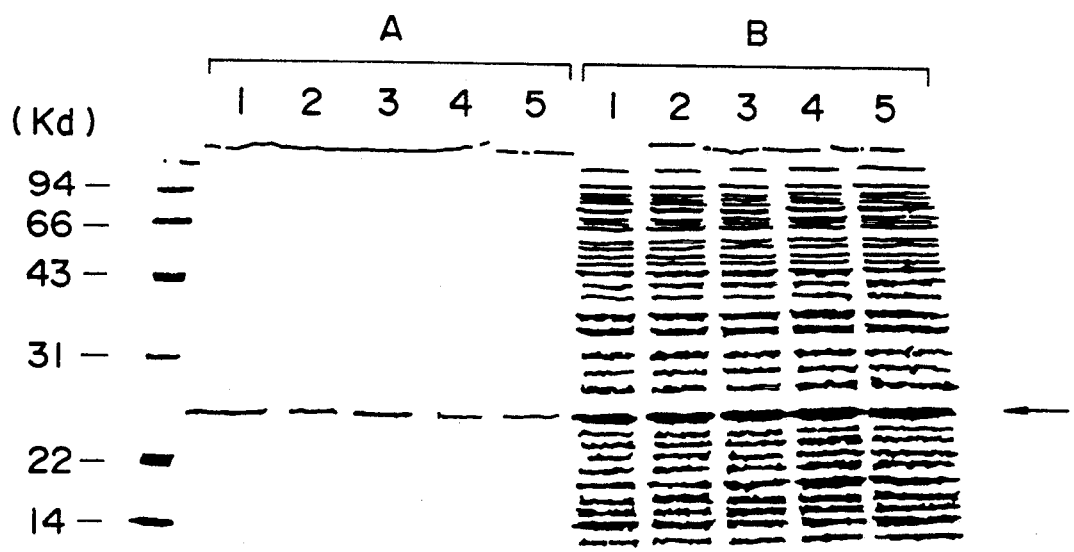

The constitution and effectiveness of the present invention will be described in more detail.

The present invention is directed to a process for secretory production of a calcium-binding protein and a biogenic substance fused with a calcium-binding protein, and can be carried out for example according to processes illustrated in Examples mentioned later.

The calcium-binding protein referred to in the process of the present invention means EF hand proteins such as calmodulin, troponin c, myosin light chain, parvalubumin, vitamin D-dependent calcium-binding proteins, S-100α, S-100β, calpactin, carpaine/CANP, oncomodulin, aequorin, etc. Further, the biogenic substance referred to herein means proteins or peptides, and biogenic substances, etc. and biogenic substances shown in Table 1 may be considered.

TABLE 1
Main biogenic peptides and their effects

| Peptides | Effects |
|---|---|
| Ameletin | Anti-acoustic stimulus memory |
| • Angiotensin I, II | Vasoconstriction, blood pressure elevation, water drive |
| • Anorexigenic factor | Anorexia |
| Apamin | Nervous poison |
| • Bombesin | Blood pressure-elevating effect, full stomach signal hormone |
| Bombinakinin 0 | Smooth-muscle striction effect |
| Bradykinins | Blood pressure depression and smooth-muscle striction effects |
| Calcitonin | Serum calcium-reducing effect, Behcet disease remedy (remedy for high calcium disease) |
| Carcinon | Blood pressure depression effect |
| Cholecystokinine-Pancreozymines | Vesica striction, pancreatic juice enzyme secretion effect |
| Contraceptive tetrapeptide | Pregnancy inhibition |
| 2-DTA, 3-DTA | Appetite control effect |
| DSIP | Hypnotic effect |
| Eledoisin | Blood pressure depression, vasodilation effects |
| α, β and γ-Endorphin | Morphine-like effect, learning, affection |
| Encephalin | Morphine-like effect, leaning, memory, appetite promotion |
| Gastrin | Promotion of gastric juice secretion |
| G H | Growth hormone, lactation promotion |
| Glucagon | Blood sugar elevation, promotion of insulin and growth hormone |
| LHRH | Sterility, cancer remedy |
| Leumorphin | Ejaculation effect |
| β, γ-Lipotropin | Lipolysis |
| Mast cell deganulation peptide | Histamine-releasing effect |
| MSHs | Perticipation in memory |
| Motilin | Gastric motion-rasing effect |
| Neurotensin | Blood pressure depression, motion promotion |
| Neuropeptide Y | Circulation control |
| PSTI | Trypsin inhibition effect |
| PDGF | Blood platelet, blood coagulation, rise of cell differentiation of wound |
| Proctolin | Excitable nervous conduction substance |
| Ranatensines | Smooth-muscle striction, pancreatic juice secretion, blood pressure elevation |
| Relaxin | Broadening of birth canal |
| Somatostatin | Growth hormone release inhibition, diabetes mellitus promotion |
| Substance P | Blood pressure depression, intestine striction, saliva secretion promotion |
| Thymopoietone I, II | Thymus T cell secretion effect |
| Thymonsine | Immunity, senility prevention |
| Tuftsine | Leucocyte, phagocytosis promotion |
| Urogastrone | Gastric juice secretion inhibition |
| Vasoactive intestinal peptide (VIP) | Blood pressure depression, vasodilation |
| Vasopressins | Uterus striction, antidiuretic |

The present invention will be described referring to the accompanying drawings.

Figures 1A, 5:
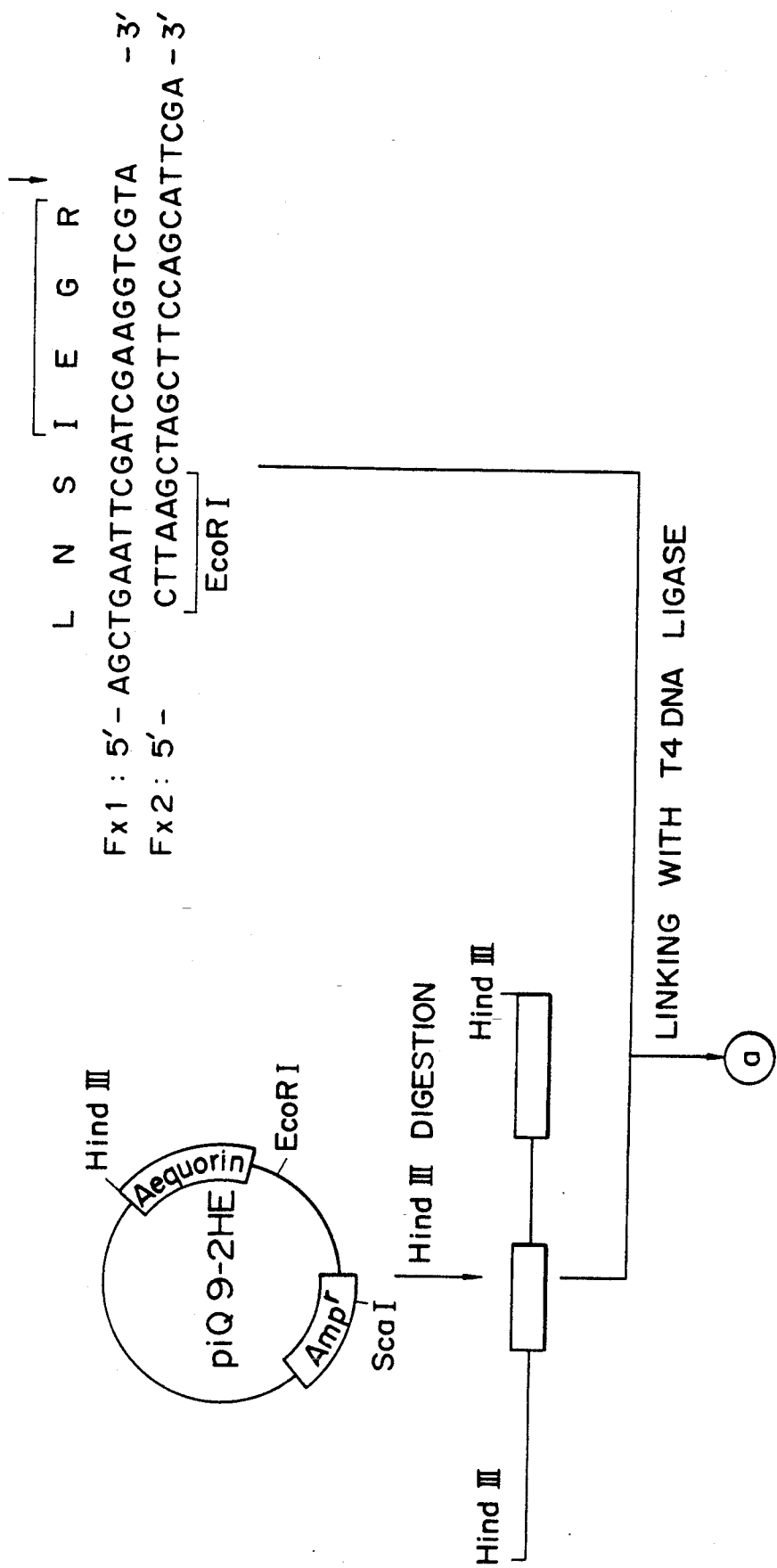
Figures 1B, 5:
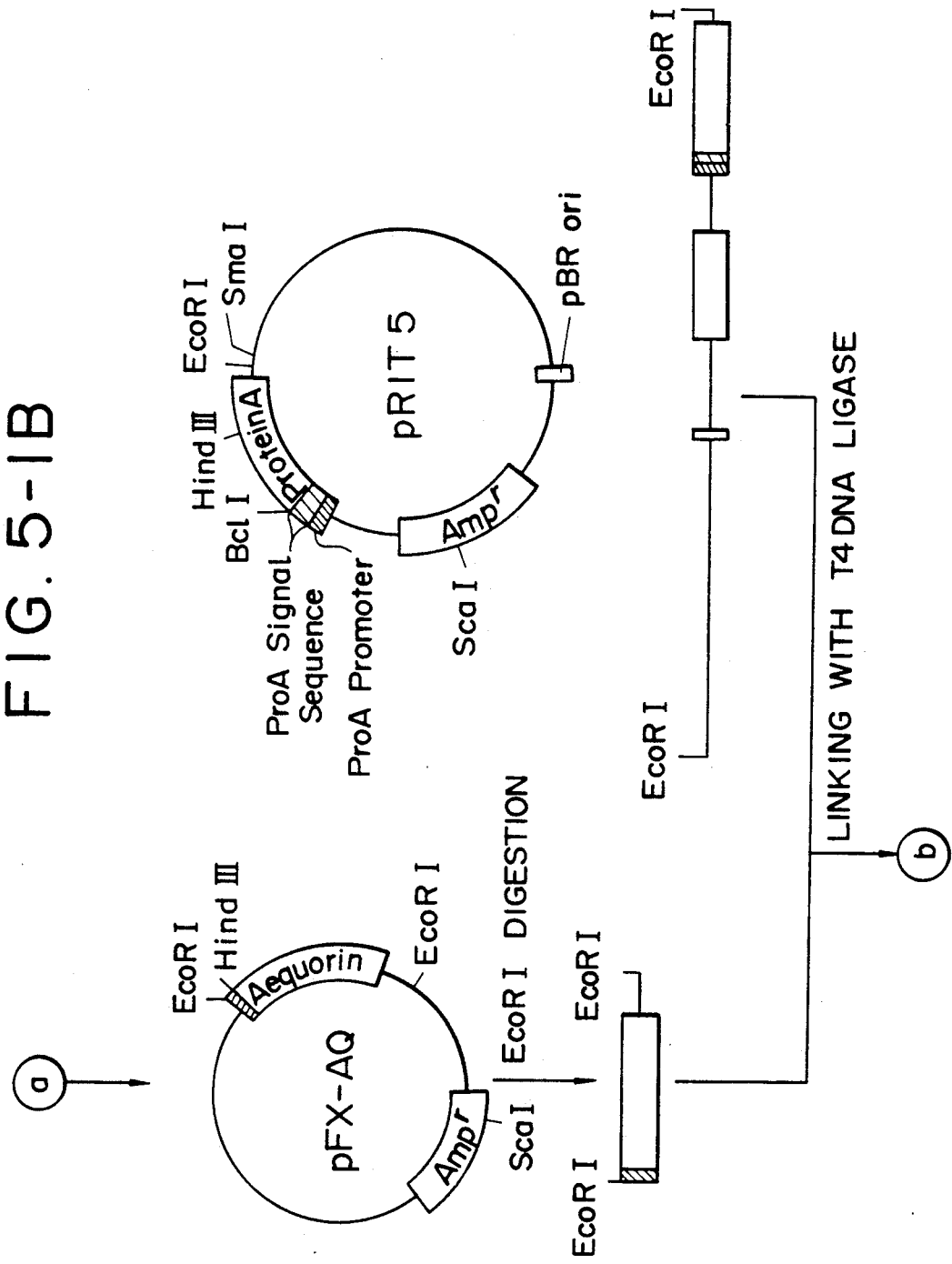

FIGS. 1A and B show construction steps of secretory expression vector of variant aequorin.

Namely, a fragment of variant aequorin gene is separated from variant aequorin expression vector piQ9-2HE (E164K, G3A, G3R, G3S), by Hind III and Bam HI digestion, followed by separating a fragment within the region containing promoter of lipoprotein, signal peptide gene of outer membrane protein A and a replication-initiating point, from aequorin secretory expression vector piP-HE (normal) (Japanese patent application laid-open No. Sho 63-102,696) by Hind III and Bam HI digestion.

By linking these fragments with T4 DNA ligase, a secretory expression vector of variant aequorin piP-HE (E164K, G3A, G3R and G3S) is prepared.

In order to indicate the direction of the material to be constructed, promoter (lpp, lac), signal sequence, ampicillin-resistant gene ($A^r$) and a few restriction enzyme sites are shown.

Figures 2A, 5:
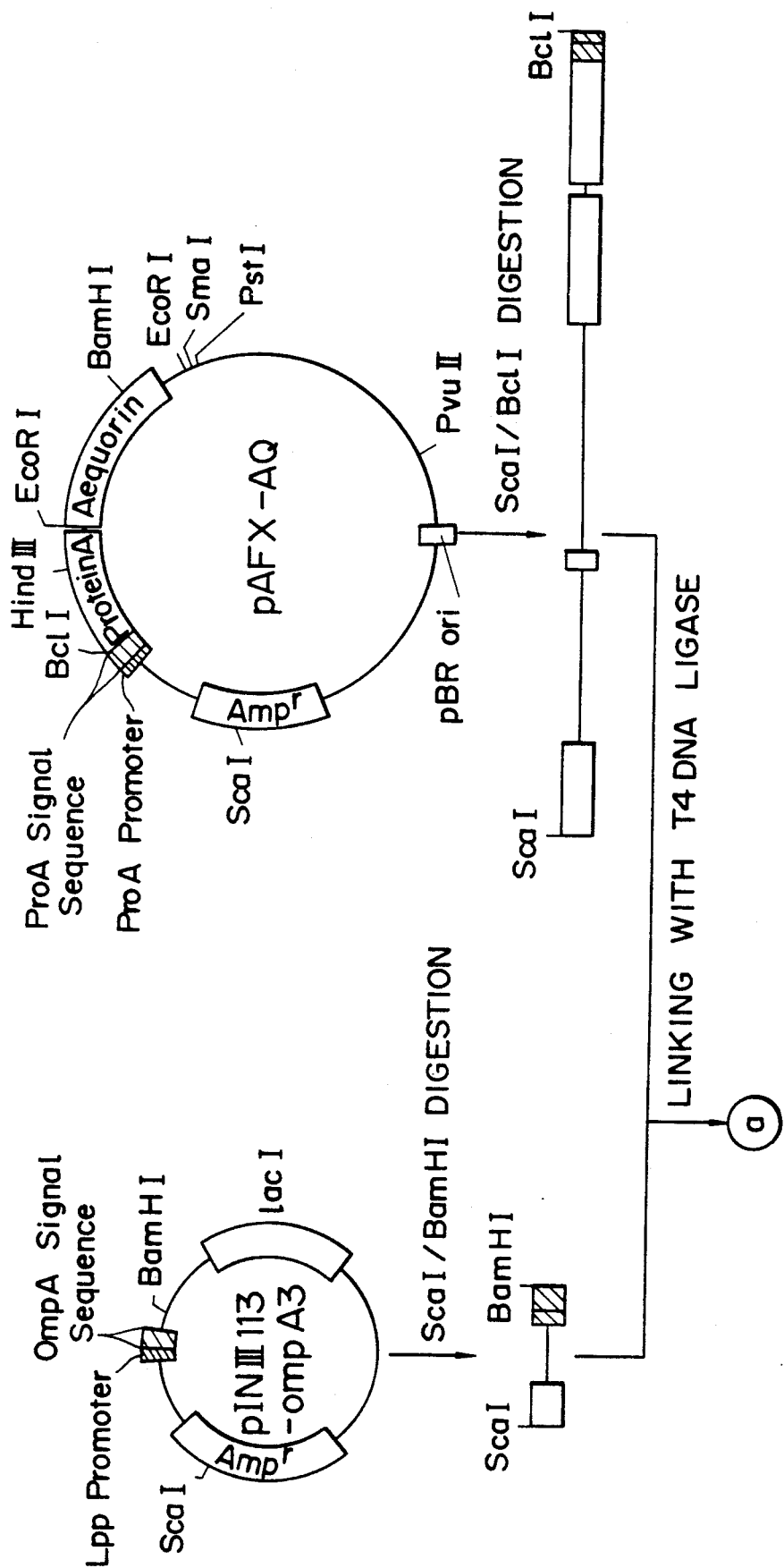
Figures 2B, 5:
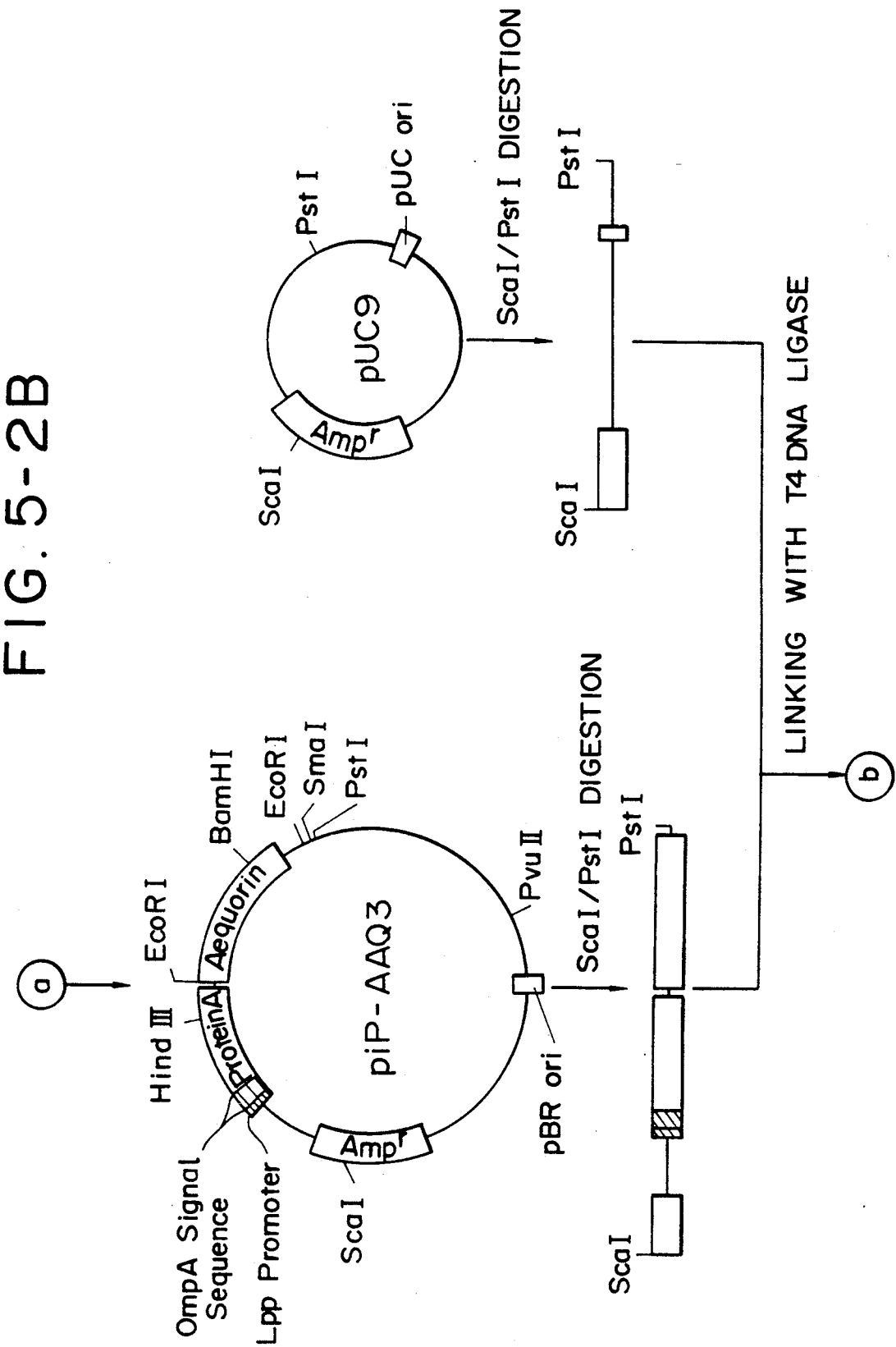
Figures 2, 2C, 5:
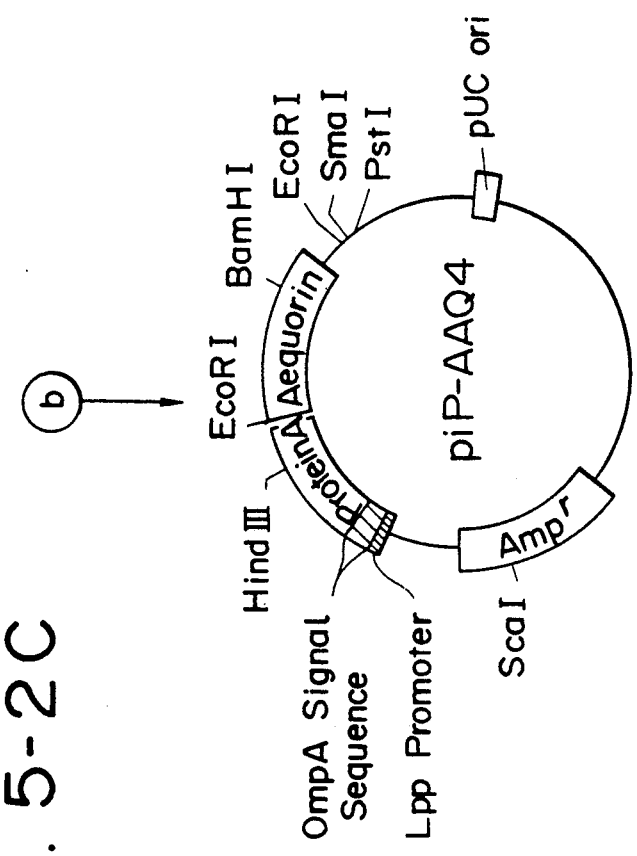

FIG. 2 shows an amino acid sequence in the vicinity of amino acid-substituted part site of EF hand region of variant apoaequorin.

FIG. 3 shows analytical results of expression and secretion of apoaequorin according to SDS-polyacrylamide electrophoresis. "A" refers to a case using the filtrate of culture and "B" refers to a case using the whole of culture.

Lane 1: piP-HE (normal)/LE 392 strain
Lane 2: piP-HE (G3A)/LE 392 strain
Lane 3: piP-HE (G3R)/LE 392 strain
Lane 4: piP-HE (G3S)/LE 392 strain
Lane 5: piP-HE (E164K)/LE 392 strain By using the secretory expression system of the present invention obtained as described above, it is considered that it has been possible to effect secretory production of calcium-binding protein and biogenic substance each in a large quantity.

EFFECTIVENESS OF THE INVENTION

The usefulness of the secretory production of useful biogenic substances utilizing the fusion with calcium-binding protein of the present invention is obvious to persons skilled in the art. Further, by using a suitable host such as *Escherichia coli*, it is possible to prepare the above protein in a large quantity. Such a host is well known to persons skilled in the art.

According to the above-mentioned disclosure, it is possible for persons skilled in the art to carry out the present invention recited in the instant patent claims. However, in order to enhance the understanding of this technique, a procedure employed for analysis of mechanism directed to the aequorin secretory production important for the present invention will be elucidated below.

EXAMPLE

EXAMPLE 1 Construction of variant aequorin secretory expression vector

Variant aequorin expression vector piQ9-2HE (E164K, G3A, G3R, G3S) (Japanese patent application No. Sho 61-245,109), Calcium Signal and Cell Response (yagi, K and Miyazaki, T. eds.) pp. 151-155, (Japan Sci. Soc. Press, Tokyo/Springer-Verlag, Berlin), was subjected to Hind III and Bam HI digestion, followed by treatment at −80° C. for 10 minutes.

Further, aequorin secretory expression vector piP-HE (Japanese patent application laid-open No. Sho 63-102,695) was subjected to Hind III and Bam HI digestion, followed by treatment at −80° C. for 10 minutes.

These treated substances were subjected to agarose gel electrophoresis, followed by recovering on a DEAE paper, a fragment having variant aequorin gene, and a fragment within the region containing a gene of signal peptide of outer membrane protein A (ompA), a promoter of lipoprotein (lpp) and a replication-initiating point (ori).

The DEAE paper was twice washed with 0.1 M NaCl, TE buffer (10 mM Tris.HCl, 1 mM EDTA, pH 8.0), followed by 4 times eluting with 1 M NaCl, TE buffer (pH 8.0), twice extracting the eluted DNA with phenol and precipitating with ethanol.

The thus obtained Hind III/Bam HI fragment of variant aequorin gene and a Hind III/Bam HI fragment containing lpp promoter, ompA signal peptide gene and ori were mixed each in a small quantity and linked with T4 DNA ligase.

A portion of the reaction solution was transformed into *Escherichia coli* LE 392, followed by spreading the resulting material on an L plate and culturing at 30° C. overnight.

The transformant was subjected to measurement of aequorin activity and further, plasmid DNA was prepared to confirm the size of the plasmid DNA, the size of inserted DNA, etc. by digestion with restriction enzyme. This corresponds to variant aequorin secretory expression vector piP-HE(E164K, G3A, G3R, G3S) shown in FIGS. 1A and B.

Resultantly, a structure obtained by replacing normal aequorin gene portion of piP-HE by variant aequorin gene has been obtained.

Variant aequorin secretory expression vector piP-HE (E164,G3A, G3R, G3S) is of a type obtained by cutting the signal peptide of ompA, and it is considered that variant apoaequorin consisting of 191 amino acid residual groups, as shown in FIG. 2, is expressed into the periplasm of *Escherichia coli*.

EXAMPLE 2 Preparation of plasmid DNA of variant aequorin secretory expression vector Colony of transformant containing variant aequorin secretory expression vector was planted on 5 ml LB medium and cultured at 30° C. overnight. The resulting culture solution (1.5 ml) was transferred into an Eppendorf's tube, followed by subjecting it to centrifuging (12,000 rpm, 2 minutes), removing the supernatant, suspending the resulting pellet in a glucose solution (60 μl) (50 mM glucose, 25 mM Tris.HCl (pH 8.0) and 10 mM EDTA), adding a 10 mg/ml lysozyme solution (40 μl) (prepared with a glucose solution just before its use), mildly mixing, allowing the mixture to stand at room temperature for 5 minutes, adding a solution of 0.2 N NaOH and 1% SDS (200 μl), mildly mixing, allowing the mixture to stand in ice for 5 minutes, adding 5M potassium acetate solution (150 μl), mildly mixing, allowing the mixture to stand in ice for at least 5 minutes, subjecting the resulting material to centrifuging (12,000 rpm, 10 minutes, 4° C.), transferring the supernatant into a separate Eppendorf's tube, once extracting with phenol, precipitating with ethanol, centrifuging (12,000 rpm, 5 minutes), washing the resulting pellet with 70% ethanol, vacuum-drying, dissolving the resulting pellet in TE buffer solution (pH 8.0) (50 μl), adding RNase A (0.5 mg/ml) solution (1 μl) so as to give a solution of 10 μl, keeping the temperature at 37° C. for 30 minutes, adding 20% polyethylene glycol (PEG) 6000/2.5 M NaCl (30 μl), sufficiently mixing, allowing the mixture to stand in ice for at least one hour, centrifuging (12,000 rpm, 5 minutes), removing the supernatant, once washing the resulting pellet with 70% ethanol, vacuum-drying, and dissolving the pellet in a suitable quantity of TE (pH 8.0).

EXAMPLE 3 Measurement of aequorin activity

The transformed strain containing varient aequorin secretory expression vector was planted on an LB medium (10 ml), followed by culturing at 30° C. overnight, preparing from this culture solution, a solution having a final concentration of 50% glycerol, preserving it at −20° C., planting the 50% glycerol stock (50 μl) on an LB medium (10 ml), culturing it at 30° C. overnight, transferring the culture solution (1.5 ml) into an Eppendorf's tube, and centrifuging (12,000 rpm, 2 minutes).

With the supernatant and the total culture solution, aequorin activity was measured as described below.

The reaction solution (200 μl) contains 30 mM Tris.HCl (pH 7.6), 10 mM EDTA (pH 7.6) buffer solution, 1 mg/ml coelenterazine (1 μl), 2-mercaptoethanol (4 μl) and raw enzyme extraction solution.

The reaction solution was allowed to stand at 4° C. overnight, followed by transferring its portion into a cuvette of a lumiphotometer (TD-4000, Laboscience Co., Ltd.), pouring 30 mM Ca Cl$_2$ (100 μl) therein and measuring its emission quantity.

EXAMPLE 4 Measurement of quantity of bacterial cells

With the culture solution obtained by culture at 30° C. overnight, described in Example 3, the quantity of bacterial cells was measured by means of Klett meter. As the filter, red filter No. 66 was used. 30 Klett units correspond to about $2 \times 10^8$ cells/ml as calculated.

The quantity of aequorin activity and the quantity of bacterial cells, of aequorin expressed and secreted from the transformant containing variant aequorin secretory expression vector are shown in Table 2.

TABLE 2

| | Expression and secretion of variant aequorin | | | |
|---|---|---|---|---|
| | Upper value: aequorin activity ($\times 10^4$ r.l.u./ml) Lower value: relative activity (%) | | | Quantity of bacterial cells (Klett unit) |
| | Supernatant of culture solution | Total culture solution | Supernatant/ total | |
| Normal | 1240 (100) | 2158 (100) | 0.57 | 206 |
| G 3 A | 303 (24) | 874 (41) | 0.35 | 210 |
| G 3 R | 1115 (90) | 1971 (91) | 0.57 | 212 |
| G 3 S | 225 (18) | 596 (28) | 0.38 | 212 |
| E164K | 753 (61) | 1404 (65) | 0.54 | 217 |

EXAMPLE 5 Analyses of expression and secretion of variant aequorin according to SDS-polyacrylamide gel electrophoresis (PAGE)

The overnight cultured solution of piP-HE (E164K, G3A, G3R, G3S/LE 392 strain) was subjected to SDS polyacrylamide electrophoresis according to Laemmli's method (Laemmli, U.K. (1970), Nature 277, 680)) for separation.

The resulting gel after the electrophoresis was dyed with Coomassie Brilliant Blue R 250, and the background was decolored. The results are shown in FIG. 3.

Lane 1 shows piP-HE (normal)/LE 392 strain, lane 2 shows piP-HE (G3A)/LE 392 strain, lane 3 shows piP-HE (G3R)/LE 392 strain, lane 4 shows piP-HE (G3S)/LE 392 strain and lane 5 shows piP-HE(E164K /LE 392 strain.

As a result of SDS-PAGE, almost no difference in the expression quantity was observed between normal aequorin and variant aequorin (see B in FIG. 3). However, as to secretion into the supernatant of the culture solution, difference was observed. Normal and G3R exhibited almost the same quantity of secretion. E35K exhibited the next more quantity of secretion. G3A and G3S exhibited the least quantity of secretion. This result shows that in spite of almost the same quantity of expression, difference in the quantity of secretion was observed. This fact is considered to originate from the change in the membrane structure of *Escherichia coli* accompanying the change in the structure of variant apoaequorin or the change in the function of variant apoaequorin.

Since the present case was carried out with variant apoaequorins having variance introduced into amino acids within the EF hand structure, it is presumed that the calcium-binding activity varies depending upon the respective variant apoaequorins.

Further, from the correlation between the proportions of aequorin activity and secretion of variant aequorin shown in Table 2, it is seen that the proportion of secretion decreases with reduction in the aequorin activity.

In view of these facts, it is suggested that secretion of apoaequorin is caused by the fact that calcium in *Escherichia coli* is accepted by apoaequorin and thereby a certain change in the structure occurs in the outer membrane of *Escherichia coli*.

In summary of the above results, the quantity of aequorin secreted to the outside of the bacterial cells of *Escherichia coli* varies in parallel to the aequorin activity, and the activity reduction of variant aequorin occurs by introducing variation into the inside of EF hand structure; thus it is presumed that secretion of aequorin occurs when aequorin accepts calcium inside the bacterial cells.

Accordingly, it is considered that such secretion of a protein to the outside of bacterial cells may similarly occur also in the case of calcium-binding protein other than aequorin.

Further, it is also suggested that a fusion protein of such a calcium-binding protein with a certain biogenic substance (protein or peptide) is also possible to effect secretory production to the outside of bacterial cells as far as the calcium-binding protein portion is not deficient in the calcium-binding activity. It goes without saying that at that time, by inserting a sequence to be specifically cut with a chemical agent or an enzyme, into the fusion region of the fusion protein, it is possible to separate the calcium-binding protein and the biogenic substance. As described above, it has been found that a protein having calcium-binding activity is possible to effect secretory production in a medium, by means of a secretory expression system using *Escherichia coli* as host, using a promoter of lipoprotein as promoter and making use of a gene of signal peptide of an outer membrane protein A. This is also advantageous for purifying the protein and effective for improving the output.

Figure 4A:
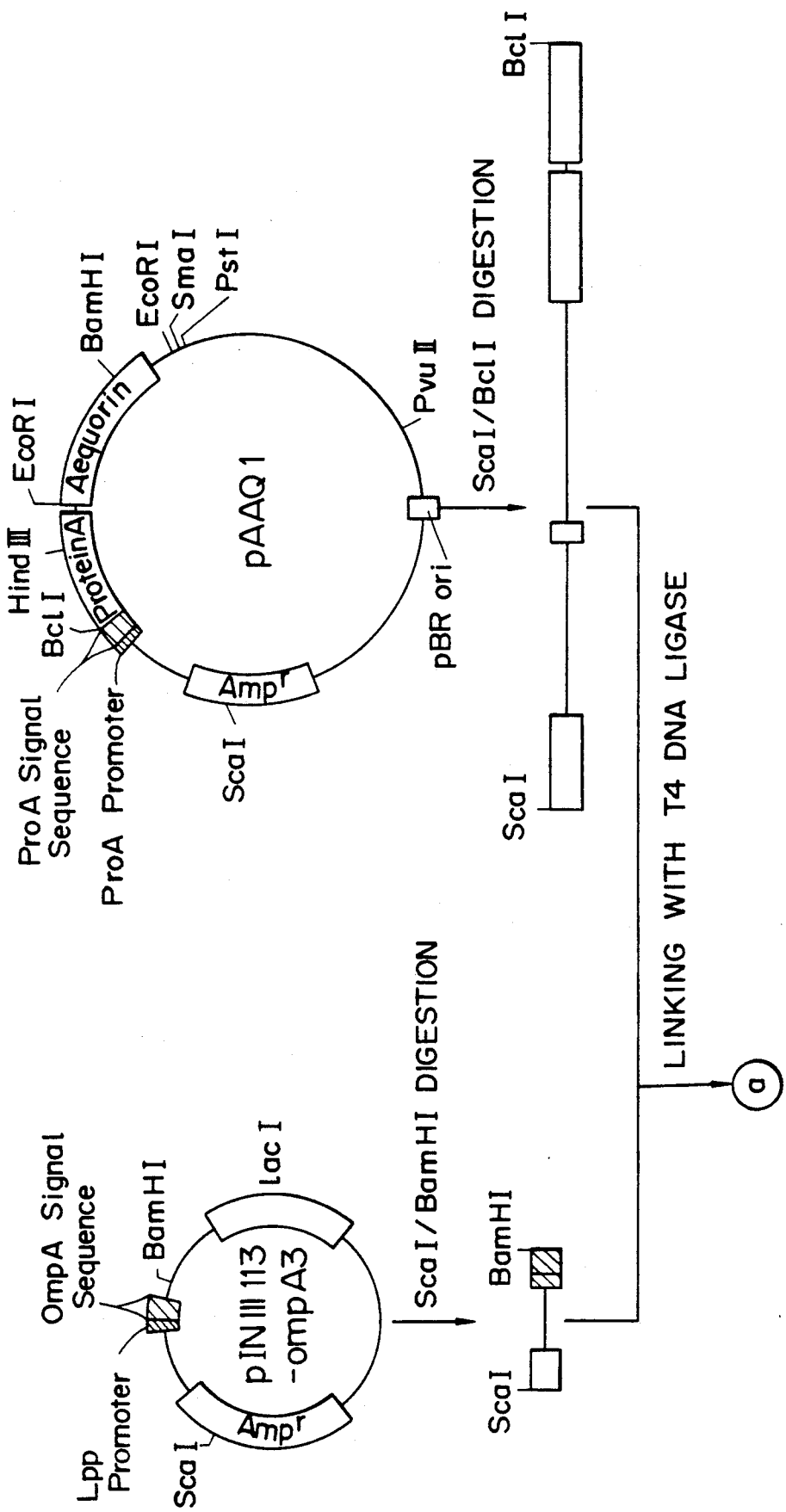
Figure 4B:
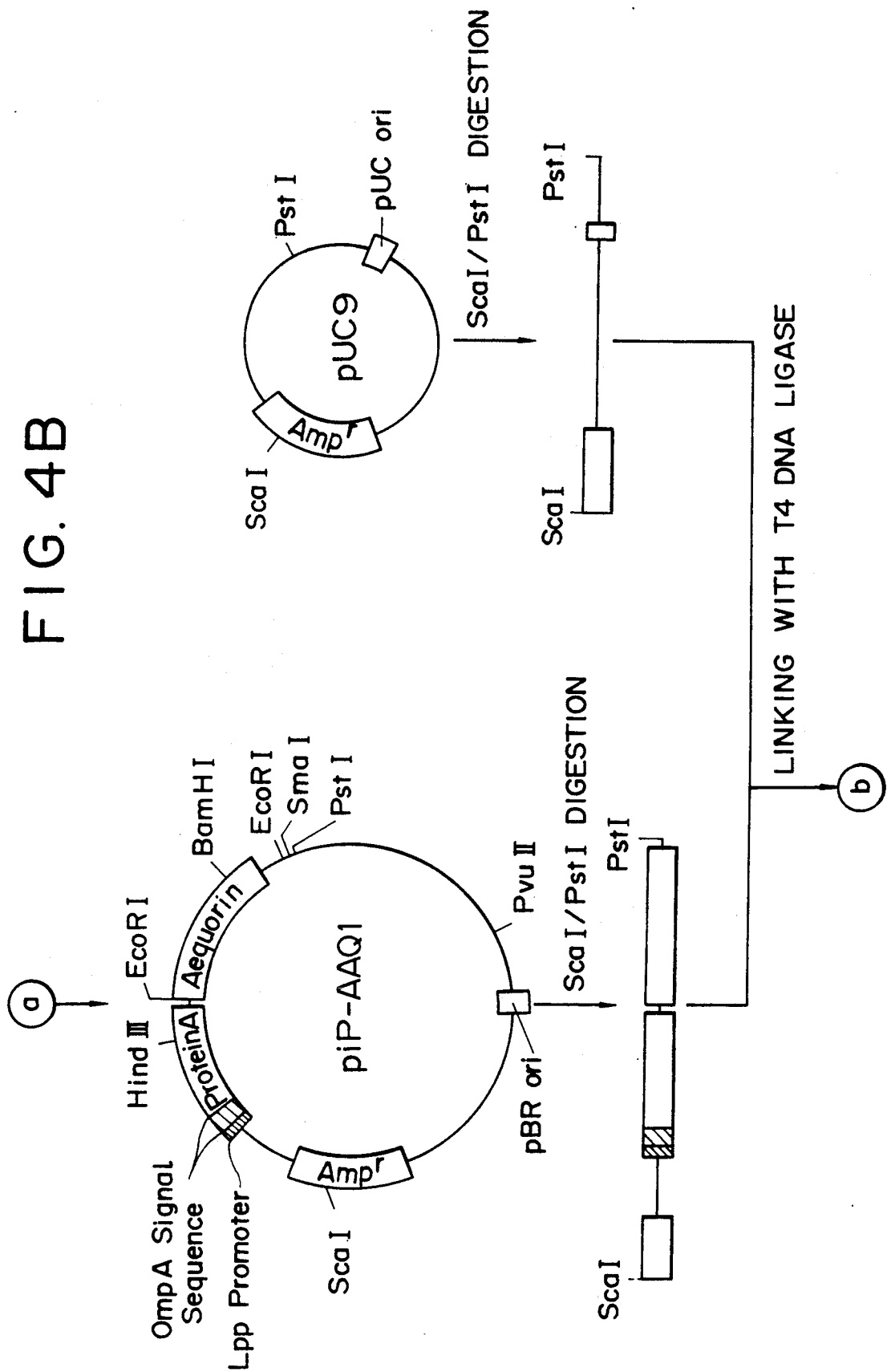
Figures 4, 4C:
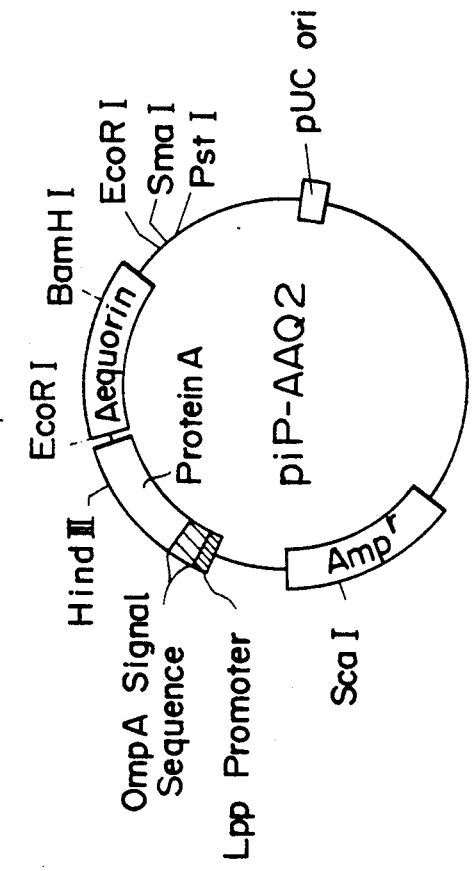

EXAMPLE 6 Construction of secretory expression vector piP-AAQ2 of a fusion protein of protein A with apoaequorin Construction of a secretory expression vector piP-AAQ2 of a fusion protein of protein A with apoaequorin was carried out as illustrated in FIGS. 4A to C.

A plasmid DNA of an expression vector pAAQ1 of a fusion protein of protein A with apoaequorin (Japanese patent application laid-open No. Sho 63-308424) was prepared in the same manner as in Example 2, followed by carrying out Sca I and Bcl I digestion, treating the resulting material at −80° C. for 10 minutes, subjecting the treated material to agarose gel electrophoresis to recover a fragment of Sca I/Bcl I containing protein A gene and pBR replication-initiating point on a DEAE paper, twice washing the DEAE paper with 0.1 M NaCl.TE buffer (10 mM Tris.HCl, 1 mM EDTA, pH 8.0), four times eluting with 1 M NaCl.TE buffer, twice extracting the eluted DNA with phenol, and precipitating with ethanol.

Further, a plasmid DNA of a secretory expression vector pIN-III 113 ompA 3 (John Ghrayeb, Hitoshi Kimura, Masayasu Takehara, Hansen Hsiung, Yoshihiro Masui and Masayori Ompiue. EMBO J.3, 2437–2442 (1984) was prepared in the same manner as in Example 2, followed by carrying out Sca I and Bam HI digestion, treating at −80° C. for 10 minutes, subjecting the treated substance to agarose gel electrophoresis, recovering a fragment of Sca I/Bam HI containing a promoter and ompA signal peptide gene on a DEAE paper, twice washing the DEAE paper with 0.1 M NaCl.TE buffer (10 mM Tris.HCl, 1 mM EDTA, pH 8.0), 4 times eluting with 1 M NaCl.TE buffer, twice extracting the eluted DNA with phenol and precipitating with ethanol.

The respective DNA fragments obtained above were mixed each in a small quantity, followed by linking them with T4 DNA ligase, transforming a portion of the reaction solution into *Escherichia coli* LE 392, spreading on an L plate containing ampicillin, culturing at 30° C. overnight, preparing plasmid DNA of the transformant in the same manner as in Example 2, and observing DNA size and restriction map by digestion with restriction enzyme to confirm that the resulting material was piP-AAQ1 shown in FIGS. 4A to C.

Further, plasmid DNA of piP-AAQ1 was subjected to Sca I and Pst I digestion, followed by treating at −80° C. for 10 minutes, subjecting the treated substance to agarose gel electrophoresis and recovering a fragment of Sca I/Pst I containing protein A gene and apoaequorin gene on a DEAE paper, twice washing the DEAE paper with 0.1 M NaCl.TE buffer (10 mM Tris.HCl, 1 mM EDTA, pH 8.0), 4 times eluting with 1 mM NaCl.TE buffer, twice extracting the eluted DNA with phenol, precipitating with ethanol, subjecting a plasmid DNA of pUC9 (Vieria, J. and Messing, J., Gene 19 259–268 (1982)) to Sca I and Pst I digestion, treating at −80° C., for 10 minutes, subjecting the treated substance to agarose gel electrophoresis, recovering a fragment of Sca I/Pst I containing pUC replication-initiating point on a DEAE paper, twice washing the DEAE paper with 0.1 M NaCl.TE buffer (10 mM Tris.HCl, 1 mM EDTA, pH 8.0)), 4 times eluting with 1 M NaCl.TE buffer, twice extracting the eluted DNA with phenol, and precipitating with ethanol.

The respective DNA fragments obtained above were mixed each in a small quantity, followed by linking them with T4DNA ligase, transforming a portion of the reaction solution into *Escherichia coli* LE392, spreading it on an L plate containing ampicillin, culturing at 30° C. overnight, preparing a plasmid DNA of the transformant in the same manner as in Example 2, and observing DNA size and restriction map with restriction enzyme digestion, whereby the resulting substance was confirmed to be piP-AAQ2 shown in FIGS. 4A to C.

It is considered that the secretory expression vector piP-AAQ2 of a fusion protein of protein A with apoaequorin secretes, in the form in which the signal peptide of ompA has been cut, fusion protein of protein A consisting of 445 amino acid residual groups with apoaequorin as shown in FIG. 4, into the periplasm of *Escherichia coli* or a medium.

FIGS. 4A to C illustrates construction of expression vector piP-AAQ2 of a fusion protein of protein A with apoaequorin.

DNA fragment of lipoprotein (Lpp) promoter and signal peptide gene (ompA) of outer membrane protein A is separated from pIN III 113 ompA-3 by Sca I/Bam HI digestion, followed by linking the fragment to DNA fragment containing a fusion gene of protein A with apoaequorin obtained from pAAQ1 by Sca I/Bcl I digestion, to prepare piP-AAQ1.

Further, pBR$_{ori}$ of piP-AAQ1 is exchanged with pUC$_{ori}$ originated from pUC9 to prepare piP-AAQ2, which is a multi-copy plasmid containing pUC$_{ori}$ and is a system for expressing a fusion protein, by placing ompA signal peptide, protein A and apoaequorin gene under the rule of Lpp promoter.

EXAMPLE 7 Construction of a secretory expression vector piP-AAQ4 of a fusion protein of protein A with apoaequorin having a cut site of factor Xa The construction of a secretory expression vector, piP-AAQ4 of a fusion protein of protein A with apoaequorin was carried out as shown in FIGS. 5-1A to C and 2A to C.

A plasmid DNA of apoaequorin expression vector piQ9-2HE (Japanese patent application No. Sho 60-280259) was prepared in the same manner as in Example 2, followed by Hind III digestion, and treating at −80° C. for 10 minutes.

Using a DNA-synthesizing instrument of an applied bio-system (ABI), FX-1 (5'-AGCTGAATTCGATC-GAAGGTCGTA-3', 24 mer) and FX-2 (5'-AGCTTACGACCTTCGATCGAATTC-3', 24 mer) were chemically synthesized. FX-1 and FX-2 were purified by OPC cartridge, followed by phosphorylating FX-1 at 5' terminal with T4DNA kinase, mixing this phosphorylated FX-1 with non-phosphorylated FX-2 each in a small quantity, and treating at 60° C. for 10 minutes.

The thus obtained respective DNA fragments were mixed each in a small quantity, followed by linking them with T4DNA ligase, transforming a portion of the reaction solution into *Escherichia coli* LE 392, spreading it on an L plate containing ampicillin, culturing at 30° C. overnight, preparing plasmid DNA with the transformant in the same manner as in Example 2, observing DNA size and restriction map by digestion with a restriction enzyme and confirming that the plasmid DNA was pFX-AQ shown in FIGS. 5-1A to C and -2A to C.

Plasmid DNA of apoaequorin expression vector pFX-AQ was prepared in the same manner as in Example 2, followed by Eco RI digestion, treating at −80° C. for 10 minutes, subjecting the treated substance to agarose gel electrophoresis, recovering Eco RI fragment containing the cut site of factor Xa and apoaequorin gene on a DEAE paper, twice washing the DEAE paper with 0.1 M NaCl.TE buffer (10 mM Tris.HCl, 1 mM EDTA, pH 8.0), 4 times eluting with 1 M NaCl.TE buffer, twice extracting the eluted DNA with phenol and precipitating with ethanol.

Further, plasmid DNA of protein A expression vector pRIT5 (Bjorn Nilsson, Lars Abrahmsen and Mathias Uhlen, EMBO J. 4, 1075–1080 (1985)) was prepared in the same manner as in Example 2, followed by Eco RI digestion and treating at −80° C. for 10 minutes.

The thus obtained, respective DNA fragments were mixed each in a small quantity, followed by linking them with T4DNA ligase, transforming a portion of the reaction solution into *Escherichia coli* GM48, spreading on an L plate containing ampicillin, culturing at 30° C. overnight, preparing plasmid DNA of the transformant in the same manner as in Example 2, observing DNA size and restriction map by digestion with restriction enzyme and confirming that the plasmid DNA was pAFX-AQ shown in FIGS. 5-1A to C and -2A to C.

Plasmid DNA of expression vector pAFX-AQ of fusion protein of protein A with apoaequorin was prepared in the same manner as in Example 2, followed by Sca I and Bcl I digestion, treating at −80° C. for 10 minutes, subjecting the treated substance to agarose electrophoresis, recovering Sca I/Bcl I fragment containing protein A gene and pBR replication-initiating point on a DEAE paper, twice washing the DEAE paper with 0.1 M NaCl.TE buffer (10 mM Tris.HCl, 1 mM EDTA, pH 8.0), 4 times eluting with 1 M NaCl.TE buffer, twice extracting the eluted DNA with phenol and precipitating with ethanol.

Further, plasmid DNA of secretory expression vector PIN-III 113 ompA-3 (John Ghrayeb, Hitoshi Kimura, Masayasu Takahara, Hansen Hsiung, Yoshihiro Masui and Masayori Inouye, EMBO J., 3, 2437–2442 (1984)) was prepared in the same manner as in Example 2, followed by Sca I and Bam HI digestion, treating at −80° C. for 10 minutes, subjecting the treated substance to agarose electrophoresis and recovering Sca I/Bam HI fragment containing promoter and ompA signal peptide gene on a DEAE paper, twice washing the DEAE paper with 0.1 M NaCl.TE buffer (10 mM Tris HCl, 1 mM EDTA, pH 8.0), 4 times eluting with 1 M NaCl.TE buffer, twice extracting the eluted DNA with phenol and precipitating with ethanol.

The thus obtained respective DNA fragments were mixed each in a small quantity, followed by linking them with T4DNA ligase, transforming a portion of the reaction solution into *Escherichia coli* LE 392, spreading it on an L plate containing amplicillin, culturing at 30° C. overnight, preparing a plasmid DNA of the transformant in the same manner as in Example 2, observing DNA size and restriction map by digestion with a restriction enzyme, and confirming that it was piP-AAQ3 shown in FIGS. 5-1A to C and -2A to C.

Further, the plasmid DNA of piP-AAQ3 was subjected to Sca I and Pst I digestion, followed by treating at −80° C. for 10 minutes, subjecting the treated material to agarose gel electrophoresis, recovering Sca I/Pst I fragment containing protein A gene and apoaequorin gene on a DEAE paper, twice washing the DEAE paper with 0.1 M NaCl.TE buffer (10 mM Tris.HCl and 1 mM EDTA, pH 8.0), 4 times eluting with 1 M NaCl.TE buffer, twice extracting the eluted DNA with phenol and precipitating with ethanol.

The plasmid DNA of pUC9 was subjected to Sca I and Pst I digestion, followed by treating at −80° C. for 10 minutes, subjecting the treated material to agarose gel electrophoresis, recovering a Sca I/Pst I fragment containing pUC replication-initiating point on a DEAE paper, twice washing the DEAE paper with 0.1 M NaCl.TE buffer (10 mM Tris.HCl and 1 mM EDTA, pH 8.0), 4 times eluting with 1 M NaCl.TE buffer and precipitating with ethanol.

The thus obtained respective DNA fragments were mixed each in a small quantity, followed by linking them with T4DNA ligase, transforming a portion of the reaction solution into *Escherichia coli*, spreading on an L plate containing ampicillin, culturing at 30° C. overnight, preparing a plasmid DNA of the transformant in the same manner as in Example 2, observing its DNA size and restriction map by digestion with a restriction enzyme and confirming that it was piP-AAQ4 shown in FIGS. 5-1A to C and -2A to C.

It is considered that the secretory expression vector piP-AAQ4 of the fusion protein of protein A with apoaequorin secretes, in a cut form of the signal peptide of ompA, a fusion protein of protein A consisting of 449 amino acid residual groups with apoaequorin as shown in FIGS. 5-1A to C and -2A to C, into the periplasm of *Escherichia coli*, or a medium.

FIGS. 5-1A to C and 5-2A to C illustrate construction of the expression vector piP-AAQ4 of the fusion protein of protein A with apoaequorin.

DNA fragments (FX1, FX2) containing a cut site of factor Xa were inserted into the Hind III site of piQ9-2HE to prepare pFX-AQ, followed by subjecting pFX-AQ to Eco RI digestion, separating DNA fragment containing factor Xa-cut site and apoaequorin gene and inserting into Eco RI site of pRIT5 to prepare pAFX-AQ.

pIN III 113 ompA-3 was subjected to Sca I/Bam HI digestion, to separate a DNA fragment containing Lpp promoter and ompA signal peptide gene, followed by exchanging the fragment with a DNA fragment containing protein A (Pro A) promoter of pAFX-AQ and protein A (Pro A) signal peptide gene, to prepare piP-AAQ3.

pBR$_{ori}$ of piP-AAQ3 was exchanged with pUC$_{ori}$ originated from pUC9 to prepare piP-AAQ4. piP-AAQ4 is basically similar to piP-AQQ2 and in the form wherein the cut site of factor Xa was inserted between protein A and apoaequorin.

Figure 6A:
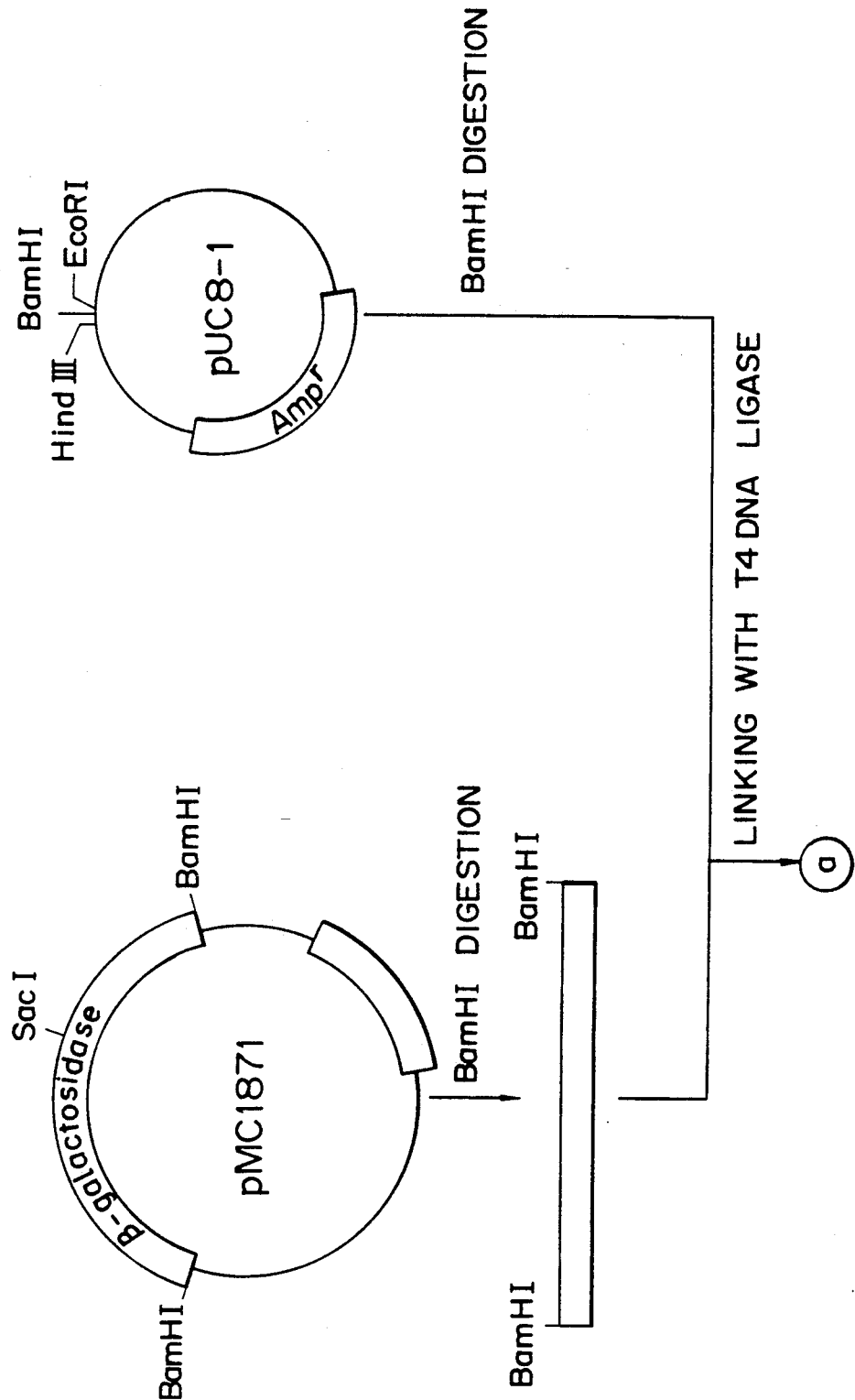
FIGS. 6A to C show the construction steps of the expression vector piP-GAQ of the fusion protein of β-galactosidase with apoaequorin.
Figure 6B:
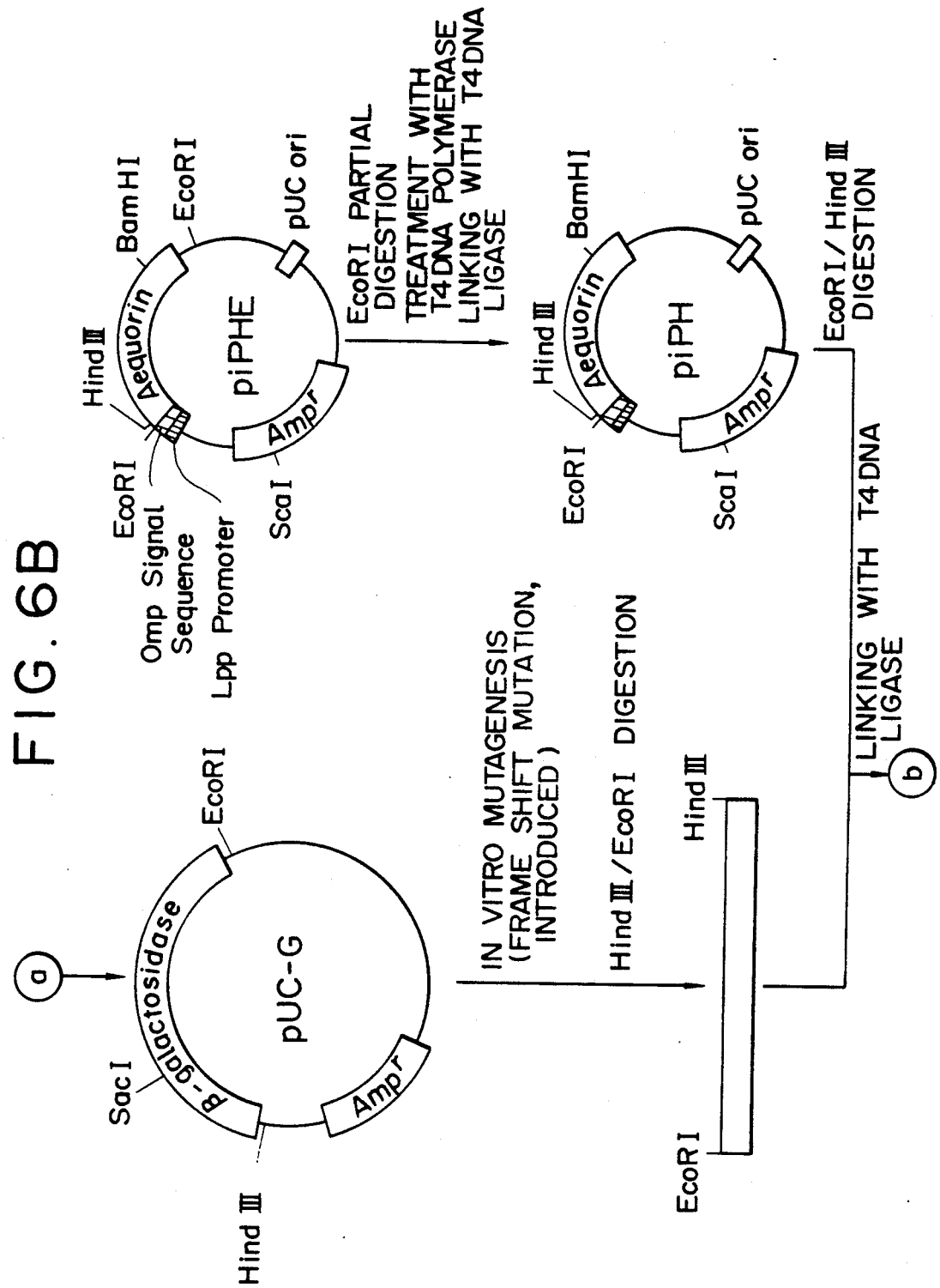
Figure 6C:
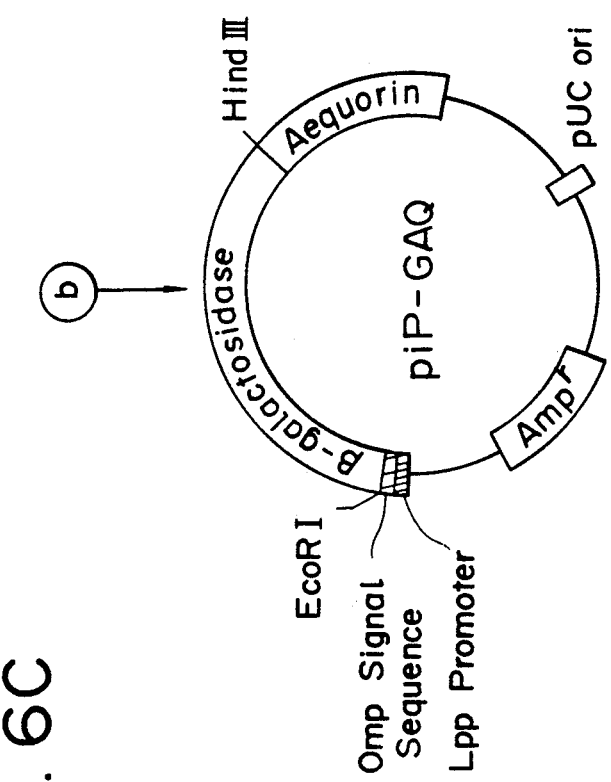

EXAMPLE 8 Construction of a secretory expression vector piP-GAQ of a fusion protein of β-galactosidase with apoaequorin The construction of a secretory expression vector piP-GAQ of a fusion protein of β-galactosidase with apoaequorin was carried out as shown in FIGS. 6A to C.

The plasmid DNA of a β-galactosidase expression vector pMC 1871 (Stuart K. Shapira, Joany Chou, Francois Malcolm J Casadaban, Gene 25, 71–82 V. Richaud and Malcolm J. Casadaban, Gene 25, 71–82 (1983)) was prepared in the same manner as in Example 2, followed by Bam HI digestion, treating at −80° C. for 10 minutes, subjecting the treated substance to agarose gel electrophoresis to recover Bam HI fragment containing β-galatosidase gene on a DEAE paper.

The DEAE paper was twice washed with 0.1 M NaCl.TE buffer (10 mM Tris.HCl, 1 mM EDTA, pH 8.0), followed by 4 times eluting with 1 M NaCl.TE buffer, twice extracting the eluted DNA with phenol and precipitating with ethanol.

The plasmid DNA of pUC8-1 (Z. Hanna, C. Fregeau, G. Prefontaine and R. Brousseau, Gene 30, 247–250 (1984)) was prepared in the same manner as in Example 2, followed by Bam HI digestion and treating at −80° C. for 10 minutes.

The thus obtained respective DNA fragments were mixed each in a small quantity, followed by linking them with T4DNA ligase, transforming a portion of the reaction solution into *Escherichia coli* JM 83, spreading it on an L plate containing ampicillin and Xgal and culturing at 37° C. overnight. Plasmid DNA of white transformant was prepared in the same manner as in Example 2, followed by observing the DNA size and the restriction map by digestion with a restriction enzyme to confirm that it was pUC-G shown in FIGS. 6A to C.

G-1 (5′-TATTATTATTTTTTGAC-3′, 17 mer) was chemically synthesized using a DNA-synthesizing instrument of Applied Bio System (ABI). G-1 was purified by OPC cartridge, and phosphorylated at 5′-terminal with T4DNA kinase.

Using commercially available site-directed mutagenesis system Mutan $^{TM}$-K (a product made by Takara Shuzo Co., Ltd.) prepared according to Kunkel method (Kunkel, T.A. (1985), Proc. Natl. Acad. Sci., USA, 82 488), a frame shift variation was introduced into galactosidase gene of pUC-G with G-1. The variation was confirmed by determining the nucleotide sequence. The galactosidase gene fragment subjected to variation treatment was subjected to Eco RI and Hind III digestion and separated.

Further, plasmid DNA of piP-HE was subjected to Eco RI digestion, followed by treating with T4DNA polymerase and treating with T4DNA ligase, to prepare piP-H having one Eco RI removed. Further, the plasmid DNA of the resulting piP-H was subjected to Eco RI and Hind III digestion.

The thus obtained respective DNA fragments were mixed each in a small quantity, followed by linking with T4DNA ligase, transforming a portion of the reaction solution into Escherichia coli LE 392, spreading on an L plate containing ampicillin, preparing plasmid DNA of the transformant in the same manner as in Example 2, observing DNA size and restriction map by digestion with a restriction enzyme and confirming that it was piP-GAQ shown in FIGS. 6A to C.

It is considered that the piP-GAQ secretes, in a cut form of signal peptide of ompA, a fusion protein of β-galactosidase consisting of 1228 amino acid residual groups as shown in FIGS. 6A to C with apoaequorin, into the periplasm of *Escherichia coli or a medium.*

FIGS. 6A to C illustrates the construction of expression vector piP-GAQ of a fusion protein of β-galactosidase with apoaequorin.

PMC1871 was subjected to Bam HI digestion, followed by separating β-galactosidase gene fragment and inserting it into the Bam HI site of pUC8-1 to prepare pUC-G. The terminal codon of β-galactosidase gene inside pUC-G was subjected to frame shift variation and removed (one A being added).

β-galactosidase gene having variation introduced therein was subjected to Eco RI/Hind III digestion and separated, followed by inserting it into Eco RI/Hind III site of piP-H obtained by removing one of two Eco RI sites of piP-HE to prepare piP-GAQ.

piP-GAQ is a multi-copy plasmid having pUC$_{ori}$ like piP-AAQ2 and piP-AAQ4, and is a system of exhibiting a fusion protein of ompA signal peptide, β-galactosidase and apoaequorin, under rule of Lpp promoter.

EXAMPLE 9 Expression and secretion of a fusion protein of protein A with apoaequorin and a fusion protein of β-galactosidase with apoaequorin With the respective transormants of the expression vectors piP-AAQ2 and piP-AAQ4 of the fusion protein of protein A with apoaequorin and the expression vector piP-GAQ of the fusion protein of β-galactosidase with apoaequorin, measurement of aequorin activity and measurement of the quantity of bacterial cells were carried out in the same manners as in Examples 3 and 4.

The quantity of aequorin activity and the quantity of bacterial cells expressed and secreted from the respective transformants are shown in the following Table 3:

TABLE 3

Expression and secretion of fusion apoaequorin

| | Upper figures: aequorin activity ($\times 10^4$ r.l.u./ml) | | | Quantity of bacterial cells (Klett unit) |
|---|---|---|---|---|
| | Supernatant of culture | whole of culture | Supernatant/ whole | |
| piP-AAQ2 | 1312 | 2602 | 0.50 | 201 |
| piP-AAQ4 | 1210 | 2512 | 0.48 | 210 |
| piP-GAQ | 380 | 1505 | 0.25 | 208 |

Figure 7:
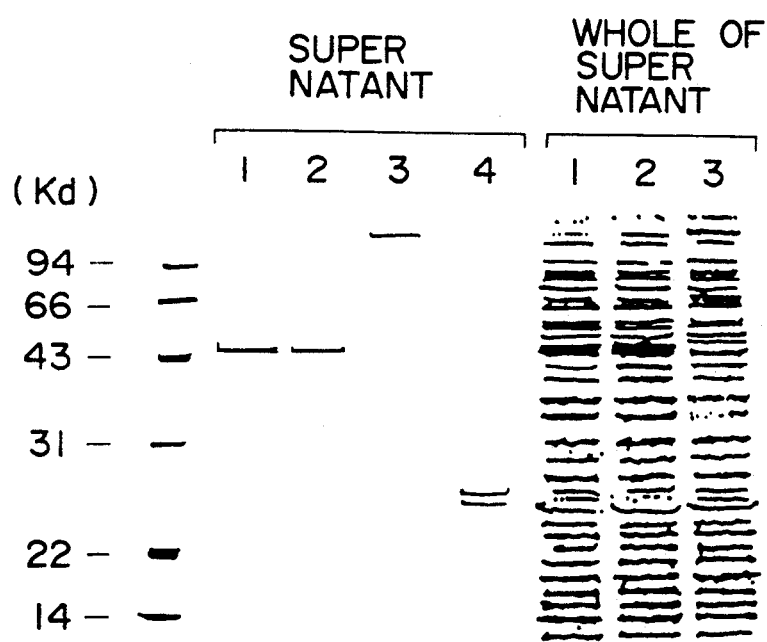

Further, with the respective samples, analysis according to SDS-DAGE was carried out in the same manner as in Example 5 (see FIG. 7). Lanes 1, 2 and 3 show piP-AAQ1 /LE 392 strain, piP-AAQ4/LE 392 strain and piP-GAQ/LE 392 strain, respectively. Lane 4 shows a substance obtained by subjecting a sample of the supernatant of piP-AAQ4/LE 392 to factor Xa treatment.

piP-AAQ2/LE 392 showed a band of 45 Kd in the culture supernatant (lane 1). It has a value slightly less than the expected molecular weight 50 Kd of fusion protein, but the band is considered as showing the fusion protein of protein A with apoaequorin.

In the case of piP-AAQ4/LE 392, too, a band of 46 Kd (lane 2) was alike detected in the supernatant. The expected molecular weight of fusion protein is 51 Kd. Further, when this fusion protein was treated with factor Xa, a band of 25 Kd (apoaequorin) and a band of 26 Kd (protein A) were detected as shown in lane 4.

As to piP-GAQ/LE 392, a band of 100 Kd or more was detected (lane 3). Since the molecular weight of the expected fusion protein is 138 Kd, this band is considered as a fusion protein of β-galactosidase with apoaequorin.

FIG. 7 shows SDS-PAGE analysis of fusion protein.

Lanes 1, 2, 3 and 4 refer to piP-AAQ2, piP-AAQ4, piP-GAQ and a factor Xa digested substance of piP-AAQ, respectively.

In any case of lanes 1, 2 and 3, a band regarded as a fusion protein is detected in the culture supernatant; hence it is seen that the secretory production of the fusion protein of apoaequorin is possible. From the result of lane 4, it is seen that the fusion protein can be separated into individual proteins.

From the results of the measurement of aequorin activity and the analysis of SDS-PAGE, it has been found that even when a separate protein such as protein A (29 Kd), β-galactosidase (117 Kd) the like is fused with apoaequorin at its amino terminal site, the aequorin activity of apoaequorin is retained, a fusion protein of a heterogenic protein with apoaequorin is produced in a large quantity with a heterogenic protein expression system in *Escherichia coli* using lipoprotein promoter and a signal peptide gene of the outer membrane protein A, and as a result, is secreted into a medium.

In view of the fact that a peptide originated from 3-amino acid linker is fused with the apoaequorin expressed from piP-HE at its amino terminal, a heterogenic protein which is fused with apoaequorin to effect secretory production has a size within a range as broad as 0 to 117 Kd; hence its application range is broad.

As seen from the foregoing, the present secretory production process is very useful for producing heterogenic proteins in *Escherichia coli* according to gene recombinant technique.

What we claim is:

1. A process for producing a fusion protein comprising a calcium-binding protein and biogenic substance of *E. coli* which facilitates the extracellular secretory production of the fusion protein, which process comprises:

preparing a recombinant plasmid as a cloning vehicle for expression of the fusion protein in *E. coli*, said plasmid comprising a first DNA sequence consisting of a lipoprotein promoter region being linked in reading phase with a second DNA sequence located downstream of said first DNA sequence, said second DNA sequence coding for a signal peptide of outer membrane protein A and being linked in reading phase with a third DNA sequence located downstream of said second DNA sequence, said third DNA sequence coding for the fusion protein, inserting said plasmid into *E. coli* to obtain a transformed *E. coli*, and cultivating the transformed *E. coli* in a suitable medium to produce said fusion protein, wherein said calcium-binding protein is selected from the group consisting of calmodulin, troponin c, myosin light chain, parvalubumin, vitamin D-dependent calcium-binding proteins, S-100, S-100β, calpactin, carpaine/CANP, and oncomodulin.

2. A process for producing a fusion protein comprising apoaequorin and a biogenic substance in *E. coli* which facilitates the extracellular secretory production of the fusion protein, which process comprises:

preparing a recombinant plasmid as a cloning vehicle for expression of the fusion protein in *E. coli*, said plasmid comprising a first DNA sequence consisting of a lipoprotein promoter region being linked in reading phase with a second DNA sequence located downstream of said first DNA sequence, said second DNA sequence coding for a signal peptide of outer membrane protein A and being linked in reading phase with a third DNA sequence located downstream of said second DNA sequence, said third DNA sequence coding for the fusion protein, inserting said plasmid into *E. coli* to obtain a transformed *E. coli*, and cultivating the transformed *E. coli* in a suitable medium to produce said fusion protein.

* * * * *